United States Patent [19]

Huybrechts et al.

[11] Patent Number: 4,985,591

[45] Date of Patent: Jan. 15, 1991

[54] ACID CATALYSTS FOR LOW TEMPERATURE CURE OF COATING COMPOSITIONS

[75] Inventors: Jozef T. Huybrechts, Oud-Turnhout, Belgium; Werner Zimmt, Bala Cynwyd, Pa.

[73] Assignee: E. I. du Pont de Nemours and Company, Wilmington, Del.

[21] Appl. No.: 233,456

[22] Filed: Aug. 15, 1988

[51] Int. Cl.$^5$ .................... C07C 143/02; C07F 9/02
[52] U.S. Cl. .................... 562/102; 562/14; 562/15; 562/103; 562/104; 562/105; 562/106; 558/155; 558/170
[58] Field of Search .......... 562/102, 14, 15, 103, 562/104, 105, 106; 558/155, 170

[56] References Cited

U.S. PATENT DOCUMENTS

| | | | |
|---|---|---|---|
| 2,914,499 | 11/1959 | Sheetz | 260/29.6 |
| 3,711,449 | 1/1973 | Brendley | 260/79.3 MU |
| 3,898,037 | 8/1975 | Lange et al. | 21/2.7 R |
| 4,001,150 | 1/1977 | Juna et al. | 260/17 R |
| 4,008,293 | 2/1977 | Maska et al. | 260/856 |
| 4,177,178 | 12/1979 | Das et al. | 260/29.40 A |
| 4,477,618 | 10/1984 | Singer et al. | 524/157 |
| 4,481,150 | 11/1984 | Ishii et al. | 562/102 |

FOREIGN PATENT DOCUMENTS

| | | |
|---|---|---|
| 1201239 | 2/1986 | Canada . |
| 1361922 | 7/1974 | United Kingdom . |
| 1413054 | 11/1975 | United Kingdom . |

OTHER PUBLICATIONS

Kinetic Parmeter Considerations for Maximizing Stability and Minimizing Cure Temperature of Thermosetting Coatings, L. Hill, J. Coatings Tech., vol. 53, No. 675, 1981.

*Primary Examiner*—Cecilia Shen
*Attorney, Agent, or Firm*—Hilmar L. Fricke

[57] ABSTRACT

Preparation of a semi-crystalline catalyst for curing coating compositions wherein an isocyanate-sulfonate or -phosphonate is made by a Michael addition followed by chain extension with an isocyanate.

5 Claims, No Drawings

ACID CATALYSTS FOR LOW TEMPERATURE CURE OF COATING COMPOSITIONS

BACKGROUND

This invention concerns acid catalysts for coating compositions which are stable for long shelf life and can be cured at relatively low temperatures.

In recent years there has been substantial work in the field of acid catalysts for low temperature cure (80°–110° C.) finishes based on hydroxyfunctional resins and "melamine" crosslinkers. Several patents have appeared such as Canadian No. 1,201,239, U.S. Pat. No. 4,477,618 Singer et al. (1984), and British No. 1,413,054 (1975) and 1,361,929 (1974), focusing on making blocked acids with low "unblocking" temperatures.

A study of L. Hill (J. Coatings Tech Vol 53, No. 675, 1981) did show that a blocked acid catalyst with both large enthalpy and entropy of activation on deblocking would be most suitable for maximizing stability and minimizing cure temperatures. His theoretical calculations showed that it would be unlikely to combine adequate shelf stability with low temperature reactivity, taking into consideration only the above mentioned kinetic effects with the unimolecular deblocking reaction as rate controlling step.

Those calculations apply for homogeneous systems in which there is no phase separation on cure and which do not take into consideration diffusion effects due to viscosity changes during crosslinking and film formation. The use of strong acids (blocked or unblocked), such as phosphoric acid and sulfonic acid derivatives, for polyol-melamine based coatings is well known and described in literature. The problems, however, remain the poor balance of shelf stability—cure temperature and curing time—overall film properties, including humidity and corrosion resistance)—compatibility with polyol and melamine crosslinker. The use of polymeric type strong acid catalysts in which 2-acrylamine-2-methylpropane sulfonic acid (AMPS) is copolymerized with other monomers to improve those properties, has been described in many patent applications.

U.S. Pat. No. 3,711,449 —Brendley (1973) teaches interpolymers of 0.2-1.0% 2-acrylamide-2-methylpropane sulfonic acid (AMPS) with other acrylates or methacrylates.

U.S. Pat. No. 3,898,037—Lange et al. (1975) teaches acrylamido-sulfonic acid polymers such as AMPS which may be copolymerized with other acrylics, and their use in corrosion inhibition.

U.S. Pat. No. 4,177,178—Das et al. (1979) teaches the use of AMPS copolymerized with other acrylics including long chain acrylics such as stearyl methacrylate, with a molecular weight of 15,000 to 100,000. These are said to be used to make thermosetting automotive topcoat paints.

U.S. Pat. No. 4,001,150—June et al. (1977) teaches the use of phosphoric or sulfonic esters, including AMPS, copolymerized with acrylics such as methacrylic acid, for use as an electroconductive resin.

U.S. Pat. No. 2,914,499—Sheetz (1959) teaches the use of various acrylic esters of sulfonic acid in emulsion polymerization.

U.S. Pat. No. 4,008,293—Maska et al. (1977) teaches the preparation of crosslinkable coating compositions containing, for instance, AMPS, as an internal crosslinking catalyst.

The problem, however, with many polymeric types of strong acid catalysts can be insufficient mobility and compatibility with the polyol-melamine binder due to viscosity change on crosslinking and film formation. Polymeric types of strong acid catalysts can also impart a strong viscosity rise due to hydrogen bonding with the other paint constituents which has a negative effect on the solids content of the final formulation. Another problem one can have with both monomeric and polymeric types of strong acid catalysts in pigmented applications is absorption on pigments and extenders which reduces the activity of the acid catalyst initially and on storage. To improve above properties it would therefore be an advantage to have the strong acid catalyst in a different phase on storage temperature, becoming available at the specific curing temperature.

Non-aqueous dispersions (NAD) are a class of polymer dispersions in which a high molecular weight (or crosslinked) core polymer is sterically stabilized by another polymer grafted or absorbed onto it. The solubility difference between grafted and/or absorbed and core polymer should be sufficient to keep the dispersion stable. Numerous patent applications describe the technology of making NAD. One could imagine the strong acid copolymerized with the core polymer composition to have it in a separate phase on storage and to become available on crosslinking due to temperature-solubility change. The problem, however, remains the polymeric nature which can give compatibility problems with the other binder constituents on crosslinking and film formation. Another problem remains the strong viscosity change and instability, since hydrogen bonding between strong-acid-in-core polymer of the NAD and hydroxy of the polyol drives the strong acid groups to the particle surface It would therefore be ideal to have a semi-crystalline dispersed monomeric or oligomeric type strong acid catalyst which becomes soluble at the specific curing temperature due to a narrow softening or melting range in which the catalyst becomes solubilized in the other paint components.

SUMMARY OF THE INVENTION

The present invention provides a process of making a semi-crystalline catalyst having the structure:

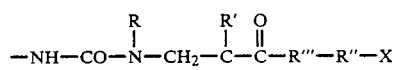

wherein X is SO₃H, PO₄RH or PO₄H₂, R" and R are the same or different and are an alkyl or aryl-alkyl chain containing 1-18 carbon atoms that may also contain hereto atoms, such as oxygen in the form of ether or hydroxy linkages or a repeating chemical unit as shown above, wherein R'" is O or NH, and wherein R' is H or methyl by the process steps of (A) Michael addition reaction of a mono functional primary amine to an α,β-unsaturated compound based on an ester or amide chemical linkage and containing a sulfonic or phosphoric acid group followed by (B) chain extension with a mono-, di- or polyfunctional isocyanate.

DETAILED DESCRIPTION

The present invention involves urea group containing dispersed strong acid which have preferably the following structure:

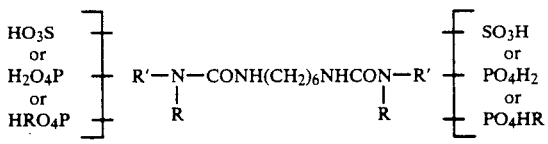

with R being an alkyl or alkyl aryl group and R' an alkyl group containing hetero atoms in the form of ester or amide.

The urea backbone is sufficiently insoluble in typical melamine-polyol-solvent composition to form a final structure finely dispersed in the formulation. If R is alkyl or aryl-alkyl, the final strong acid dispersion becomes soluble enough at temperatures above 80° C. to finally provide a monomeric or oligomeric acid catalyst which is soluble in the other binder constituents.

The evaluation in a typical high solids clear coat formulation which contains a low molecular weight acrylic polyol and either a reactive (Cymel 325 from Cyanamide) or a fully alkylated (Cymel 303) melamine showed an acceptable balance of oven (49° C.) and shelf stability with sufficient cure at bakes of 30 minutes at 80°-110° C. The curing speed was evaluated based on hardness, flexibility measurements and solvent resistance results.

Film clarity and flow were excellent even when baked at 80° C., which shows that the partially crystalline acid catalyst does go into solution on film formation and cure.

The technology is based on simple reactions and raw materials. In a first step a secondary amine functional acid is made via conjugate addition of a monofunctional amine to AMPS neutralized with a tertiary amine.

e.g. 1 mol AMPS
1 mol TEA (triethylamine)
Add 1 mol of LA (laurylamine) in refluxing isopropanol.

In a second step a reaction product is formed by reaction of 2 mols of previous adduct with 1 mol of HDI (hexamethylene diisocyanate) under high shear conditions in the binder we want to modify. The balance of oleophilicity and crystallinity in the structure generally determine the balance of potlife and final film properties. It is known that ureas are nucleophilic enough to react with melamine crosslinkers so these catalyst might also give a better performance balance for humidity resistance.

The Michael addition reaction of primary amine to an α,β-unsaturated compound is preferably run in solution in an active solvent. The solvent can be e.g. alcohol, ketone, aliphatic, water, ether or aromatic, ester solvent or blend and can be run at reflux or lower conditions. The equivalent ratio of amine to ethylenic unsaturated bond can be between 10/1 to 1/10 but is preferably stoichiometric.

Examples of mono-primary amines are methylamine, propylamine, octylamine, laurylamine, benzylamine, ethanolamine, polyethyleneoxide monoamines and polypropyleneoxide monoamines. Examples of di-primary amines are ethylenediamine, hexane-1,6-diamine, polyethyleneoxidediamines, polypropyleneglycoldiamines and xylylenediamine. Although the reaction is preferably run with mono- or diamines, polyfunctional amines can be used. The chemical structure of the amine will finally determine the compatibility and crystallinity of the dispersed acid catalyst after chain extension.

The chain extension can be run with mono-, di- or polyisocyanates as, e.g., monoisocyanates: methylisocyante, hexylisocyanate, toluene monoisocyanate, diisocyanates: 1,6-hexamethylenediisocyanate, dodecane diisocyanate, trimethylhexamethylenediisocyanate, toluene diisocyanate, dicyclohexylmethane diisocyanate (Desmodur W) from Bayer, or xylylene diisocyanate; polyisocyanates: Biuret of hexamethylenediisocyanate (Desmodur N), or Cyclotrimer of hexamethylenediisocyanate (Desmodur 3390). Preferably symmetrical diisocyanates are used and more preferably hexamethylenediisocyanate. The reaction of the amine-acid adduct formed in the first step can be run in situ with the diisocyanate after which the reaction product can be dispersed in the final binder. Preferably the chain extension is run in presence of the binder under shear conditions. The formation of the urea adduct on reaction with the amine-acid under high shear forms in situ particles which are dispersed in the binder of choice.

In the Examples, parts, proportions and ratios are by weight except where indicated otherwise.

EXAMPLE 1

To a 500 ml reactor equipped with stirrer, condenser were added:

| propylamine | 40.88 |
|---|---|
| isopropanol (IP) | 17.53 |

Mixture was brought at slight reflux.
To the solution was added over 30 min a solution of:

| 2-Acrylamido-2-methylpropane sulfonic acid (AMPS) (Lubrizol 2401) | 143.41 |
|---|---|
| Triethylamine (TEA) | 69.67 |
| IP | 128.17 |
| t-Butylcatechol (t-BC) | 0.04 |

After the addition the solution was held 90 min at reflux. NMR run on the dried reaction product in dimethylsulfoxide showed structure:

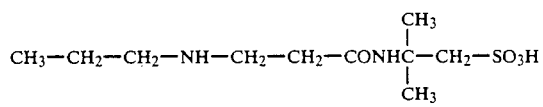

In an analogous way as in Example 1, the following adducts were prepared. The molar ration TEA/amine/AMPS was 1/1/1.

| Example (mols) | 2 | 3 | 4 | 5 | 6 |
|---|---|---|---|---|---|
| Octylamine | 1 | | | | |
| Laurylamine | | 1 | | | |
| Oleylamine | | | 1 | | |
| Benzylamine | | | | 1 | |
| Ethanolamine | | | | | 1 |
| AMPS | 1 | 1 | 1 | 1 | 1 |
| TEA | 1 | 1 | 1 | 1 | 1 |

All reaction products have NMR spectra expected from amine addition to the α,β-unsaturated bond.

EXAMPLE 7

To a 500 ml flask equipped with a high speed stirrer was added.

| Example 1 | 339.8 |
|---|---|

With stirring after solution was added:

| Hexamethylenediisocyanate | 32.6 |
|---|---|
| Ethylacetate | 32.6 |

The addition caused the temperature of the reaction mixture to rise from 25° C. to 42° C. After 45 min the isocyanate absorption in IR has disappeared. The reaction product was insoluble in most common solvents. Elemental analysis and mass spectrometry of the product agreed with following chemical structure:

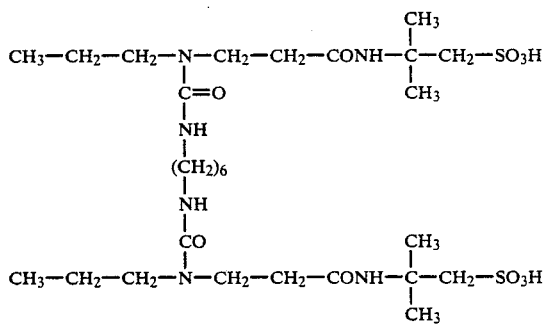

In an analogous way as in Example 7, the following adducts were prepared. The molar ration of compounds described in Examples 2-6 to hexamethylenediisocyanate was 2 to 1. Elemental analysis confirmed a chemical composition as shown above but replacing the propyl group with the appropriate chemical group in the amine adduct.

| Example (mols) | 8 | 9 | 10 | 11 | 12 |
|---|---|---|---|---|---|
| Adduct Example 2 | 2 | | | | |
| Adduct Example 3 | | 2 | | | |
| Adduct Example 4 | | | 2 | | |
| Adduct Example 5 | | | | 2 | |
| Adduct Example 6 | | | | | 2 |
| Hexamethylene-diisocyanate | 1 | 1 | 1 | 1 | 1 |

In a following set of experiments the synthesis of the adducts as described in Examples 7-12 was done in presence of an acrylic resin 72% solids in Solvesso 100 from Exxon, hydroxyl value 145, $\overline{Mn}=1700$ $\overline{Mw}=3500$. The reaction product of the acid functional amine with the diisocyanate was formed under shear and the formed urea was finely dispersed in the acrylic binder. The mixture was stirred until the isocyanate has disappeared as determined by IR. Molecular weight determination of the unmodified acrylic resin control versus different samples containing the dispersed semi-crystalline catalysts showed the two to be identical, which indicated the isocyanate has not reacted with the acrylic binder. The particles of Example 8 and 10 were centrifuged, washed and dried, and elementary analysis proved the above chemical structure.

|  | Example 8 | | Example 10 | |
|---|---|---|---|---|
|  | theoretical | found | theoretical | found |
| % S | 7.3 | 7.1 | 5.7 | 5.7 |
| % C | 53.2 | 55 | 60.3 | 62.4 |
| % N | 12.4 | 11.6 | 9.7 | 8.6 |

From above mentioned Example 8-12 clear solutions were prepared by mixing the Cymel 325 from Cyanamid which is a partially methylated melamine resin. The ratio of acrylic/melamine=70/30 by weight. A control was included in these tests which contained amine blocked p-toluenesulfonic acid (PTSA) and a control containing no acid. All samples were diluted to 50% weight solids with n-butanol and were adjusted to contain the same molar amount of sulfonic acid (0.045 mol). Draw downs on glass were prepared and baked 30 min at 100° C.

Results:

|  | Example | | | | | control with PTSA | control no sulfonic acid |
|---|---|---|---|---|---|---|---|
|  | 8 | 9 | 10 | 11 | 12 | | |
| film build (microns) | 79 | 80 | 79 | 78 | 79 | 70 | too soft too measure |
| Knoop hardness | 5.6 | 10.9 | 15.1 | 8.8 | 7.8 | 3.3 | |

In another set of experiments Cymel 303 was used which is a fully methylated melamine resin from Cyanamid. The ratio was also 70/30 acrylic melamine and the solutions were diluted to 50% weight solids using n-butanol.

|  | Example | | | | | control with PTSA | control no sulfonic acid |
|---|---|---|---|---|---|---|---|
|  | 8 | 9 | 10 | 11 | 12 | | |
| film build (microns) | 72 | 79 | 83 | 80 | 73 | 75 | too soft to measure |
| Knoop hardness | too soft | 3.2 | 5.7 | 3 | 1.4 | 1.6 | |

All samples containing the dispersed acid catalyst remained stable for several weeks, exhibiting no viscosity change.

What is claimed is:

1. A process making a semi-crystalline catalyst having the structure:

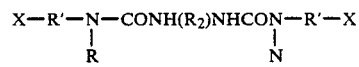

where X is $SO_3H$, $PO_4H$, or $PO_4H_2$, R is H or methyl and R' is an alkylene group containing hetero atoms in the form of ester or amide and $R_2$ is an alkylene group by the process of steps of (A) Michael addition reaction of a mono functional primary amine to an $\alpha,\beta$-unsaturated compound based on an ester or amide chemical linkage and containing a sulfonic or phosphoric acid group followed by (B) reaction with a di- or polyfunctional isocyanate.

2. The process of claim 1 wherein the sulfonic or phosphoric acid group is fully or partially neutralized with an amine.

3. The process of claim 1 wherein the α,β-unsaturated compound contains an amide linkage.

4. The process of claim 1 wherein the amine compound is a monofunctional primary amine based on an alkyl, aryl-alkyl chain.

5. The process of claim 1 wherein the isocyanate compound is an aliphatic or cycloaliphatic diisocyanate.

* * * * *

UNITED STATES PATENT AND TRADEMARK OFFICE
CERTIFICATE OF CORRECTION

PATENT NO. : 4,985,591

DATED : January 15, 1991

INVENTOR(S) : Jozef T. Huybrechts, Werner Zimmt

It is certified that error appears in the above-identified patent and that said Letters Patent is hereby corrected as shown below:

Claim 1. Column 6, lines 55-57, delete structural chemical formula and insert the following formula:

Signed and Sealed this

Second Day of November, 1993

Attest:

BRUCE LEHMAN

Attesting Officer     Commissioner of Patents and Trademarks